(12) United States Patent
Windram

(10) Patent No.: US 11,896,244 B2
(45) Date of Patent: Feb. 13, 2024

(54) METHOD OF REPAIRING PLANTAR PLATE TEARS THROUGH GRAFT AUGMENTATION

(71) Applicant: Warren W. Windram, Fort Lauderdale, FL (US)

(72) Inventor: Warren W. Windram, Fort Lauderdale, FL (US)

(73) Assignee: Warren Windram, Aventura, FL (US)

( * ) Notice: Subject to any disclaimer, the term of this patent is extended or adjusted under 35 U.S.C. 154(b) by 283 days.

(21) Appl. No.: 17/397,624

(22) Filed: Aug. 9, 2021

(65) Prior Publication Data

US 2021/0361301 A1    Nov. 25, 2021

Related U.S. Application Data

(62) Division of application No. 16/357,295, filed on Mar. 18, 2019, now Pat. No. 11,083,472.

(Continued)

(51) Int. Cl.
| | |
|---|---|
| *A61B 17/17* | (2006.01) |
| *A61F 2/08* | (2006.01) |
| *A61F 2/42* | (2006.01) |
| *A61B 17/16* | (2006.01) |
| *A61B 17/84* | (2006.01) |

(Continued)

(52) U.S. Cl.
CPC ...... *A61B 17/1775* (2016.11); *A61B 17/1682* (2013.01); *A61B 17/1714* (2013.01); *A61B 17/848* (2013.01); *A61F 2/0805* (2013.01); *A61F 2/0811* (2013.01); *A61F 2/4225* (2013.01); *A61B 17/0206* (2013.01); *A61B 90/11* (2016.02); *A61B 2017/681* (2013.01); *A61B 2090/061* (2016.02); *A61B 2090/067* (2016.02)

(58) Field of Classification Search
CPC ............ A61B 17/1775; A61B 17/1714; A61B 17/1682
See application file for complete search history.

(56) References Cited

U.S. PATENT DOCUMENTS

| | | |
|---|---|---|
| D505,205 S | 5/2005 | Freid |
| 9,138,246 B2 | 9/2015 | Anderson et al. |

(Continued)

FOREIGN PATENT DOCUMENTS

| | | | |
|---|---|---|---|
| CA | 2836648 A1 * | 6/2014 | ............ A61B 17/17 |
| CA | 2836648 A1 | 6/2014 | |

*Primary Examiner* — Christian A Sevilla
(74) *Attorney, Agent, or Firm* — Mark C. Johnson; Johnson Dalal

(57) ABSTRACT

A method of repairing plantar plate tears of an individual through augmentation that includes cutting an incision above a damaged area of a plantar plate on an individual, spreading the tissue with a plantar plate joint distractor, inserting a drill insertion member into the plantar drill guide and at a drilling angle over tissue at or near the damaged area of the plantar plate, drilling, with a drill bit and at the drilling angle, into the tissue at or near the damaged area of the plantar plate, attaching a K-wire to a graft, pulling, with the K-wire, the graft across a damaged area of the plantar plate augmenting the damaged area of the plantar plate, and manipulating an interference-type screw through the plantar plate and either or both the K-wire and the graft to engage and compress the graft for fixation.

9 Claims, 17 Drawing Sheets

Related U.S. Application Data

(60) Provisional application No. 62/644,401, filed on Mar. 17, 2018.

(51) Int. Cl.
    *A61B 17/68* (2006.01)
    *A61B 17/02* (2006.01)
    *A61B 90/00* (2016.01)
    *A61B 90/11* (2016.01)

(56) References Cited

U.S. PATENT DOCUMENTS

| | | | |
|---|---|---|---|
| 9,241,784 B2* | 1/2016 | Fallin | A61B 17/1739 |
| 10,335,220 B2* | 7/2019 | Smith | A61B 17/1739 |
| 2003/0097131 A1* | 5/2003 | Schon | A61B 17/7233 |
| | | | 606/62 |
| 2003/0216742 A1* | 11/2003 | Wetzler | A61B 17/17 |
| | | | 606/96 |
| 2010/0121325 A1* | 5/2010 | Tyber | A61B 17/8061 |
| | | | 606/62 |
| 2011/0184528 A1* | 7/2011 | Beckendorf | A61F 2/4225 |
| | | | 623/23.42 |
| 2011/0257652 A1* | 10/2011 | Roman | A61B 17/16 |
| | | | 606/62 |
| 2013/0023988 A1* | 1/2013 | Sinnott | A61B 17/06166 |
| | | | 623/13.14 |
| 2013/0184818 A1* | 7/2013 | Coughlin | A61B 17/0206 |
| | | | 623/13.14 |
| 2014/0180348 A1 | 6/2014 | Thoren et al. | |
| 2014/0243838 A1* | 8/2014 | Feibel | A61B 17/921 |
| | | | 606/96 |
| 2015/0157339 A1* | 6/2015 | McGinley | A61B 17/15 |
| | | | 606/87 |
| 2015/0257899 A1* | 9/2015 | Luna | A61B 17/15 |
| | | | 623/21.18 |
| 2016/0000490 A1 | 1/2016 | Kartalian et al. | |
| 2017/0164989 A1* | 6/2017 | Weiner | A61B 17/8061 |
| 2019/0336140 A1* | 11/2019 | Dacosta | A61B 17/15 |
| 2021/0045732 A1* | 2/2021 | Allard | A61F 2/08 |
| 2021/0068815 A1* | 3/2021 | Summitt | A61B 17/1682 |

\* cited by examiner

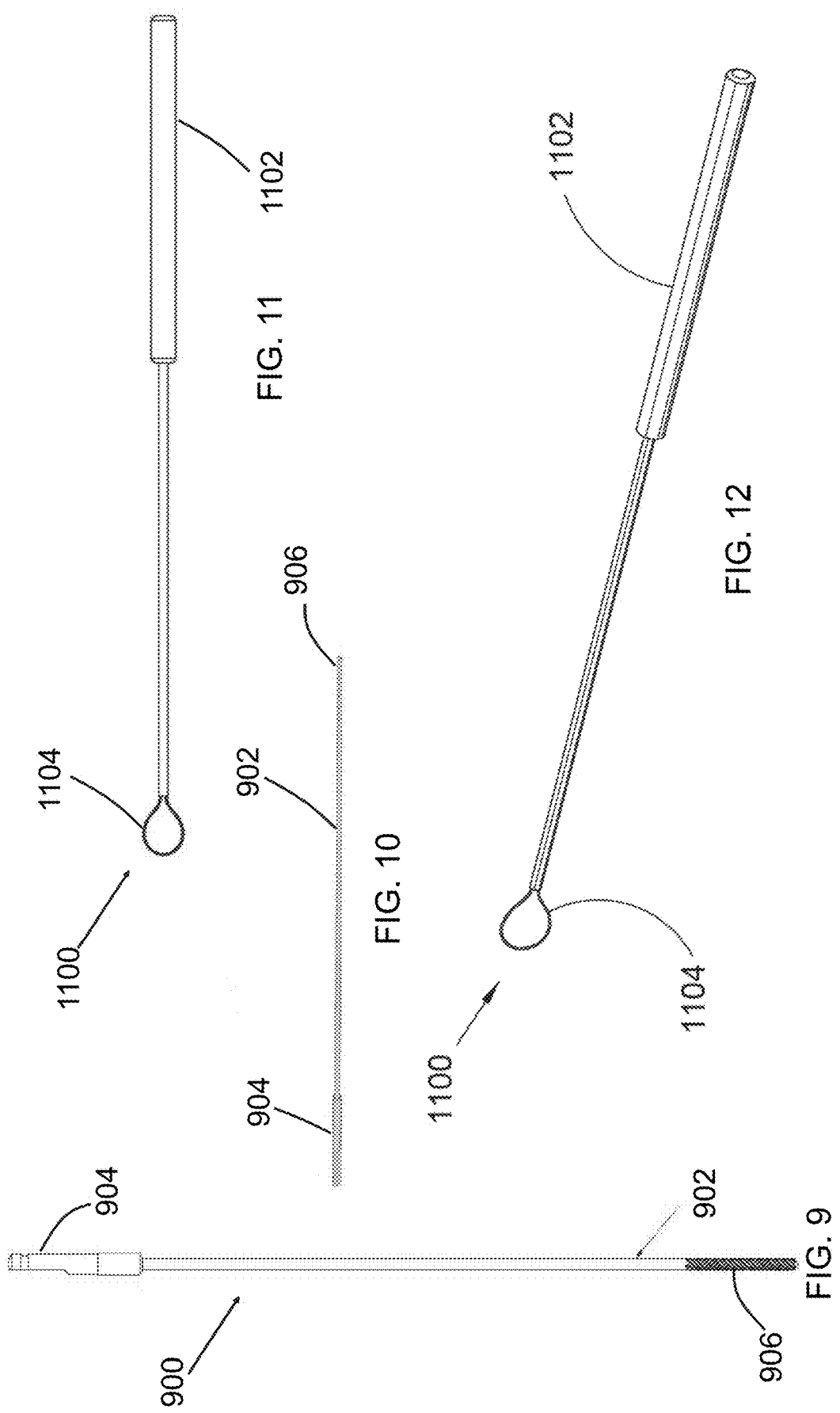

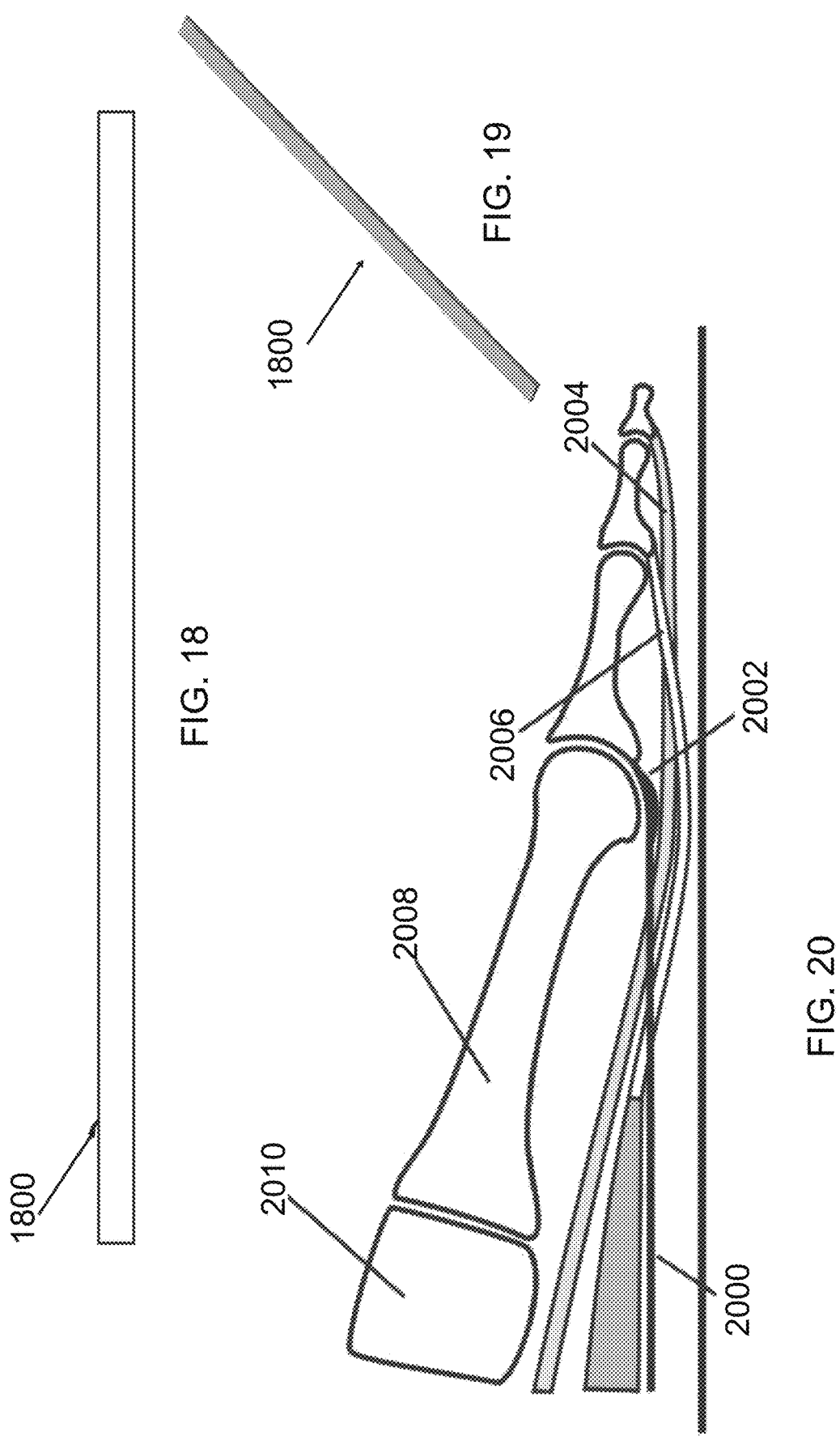

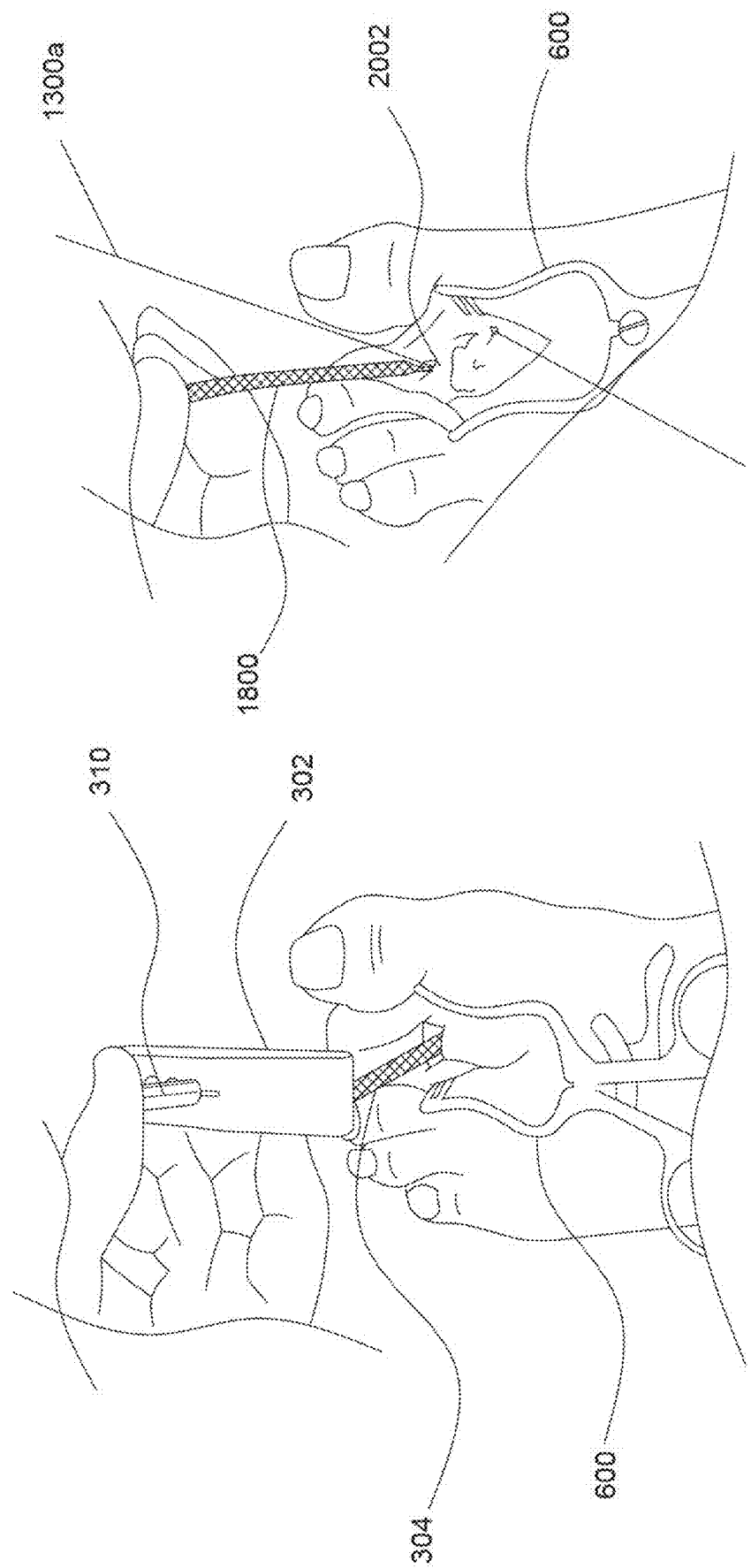

METHOD OF REPAIRING PLANTAR PLATE TEARS THROUGH GRAFT AUGMENTATION

FIELD OF THE INVENTION

The present invention relates generally to a plantar plate augmentation kits and assemblies and method of repairing plantar plate tears through augmentation, and, more particularly, relates to a kit assembly and method that repairs plantar plate tears through use of an FDA approved soft tissue graft that augments the plantar plate structure through use of a plantar plate drill guide, a plantar plate joint distractor, at least two K-wires, a drill bit, a graft passer, at least two interference-type screws, a screw driver, and a soft tissue graft.

BACKGROUND OF THE INVENTION

It is known in the art that the plantar fascia is the flat band of tissue (ligament) that connects the heel bone to the toes. The plantar fascia supports the arch of your foot. If a person strains the plantar fascia, it gets weak, swollen, and irritated. Consequently, the heel or the bottom of the foot hurts when standing or walking.

Generally, the plantar plate is a ligament that is situated on the underside of the metatarsal phalangeal joints at the ball of the feet. A plantar plate tear is a common injury of the forefoot which is caused by repetitive overload.

The plantar plate is a fibrocartilaginous tissue that is the direct insertion of the plantar fascia into the base of the phalanges of the lesser toes. Plantar plate injuries are a common foot condition that has been a challenging procedure for physicians to master. Traditionally, there are complicated suture-based repair techniques that are difficult to perform and are based on a suture repair, and not graft augmentation.

To aid in overcoming surgical challenges associated with plantar plate injuries, the present invention provides a planter plate graft augmentation kit, assembly, and method of use. Specifically, in one embodiment, the kit described below, which may be designed for single use by a physician, is designed to provide a surgeon a fast, easy, and effective way to repair the plantar plate tear. This technique uses an FDA approved soft tissue graft that augments the plantar plate structure.

Therefore, a need exists to overcome the problems with the prior art as discussed above.

SUMMARY OF THE INVENTION

The invention provides a single-use plantar plate augmentation kit assembly and method of repairing plantar plate tears through augmentation that overcomes the hereinaforementioned disadvantages of the heretofore-known devices and methods of this general type and that provides an assembly of tools used to augment a plantar plate with a soft tissue graft, and specifically an Artelon graft.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient plantar plate augmentation kit assembly and method of repairing plantar plate tears through augmentation. Embodiments of the invention provide a plantar plate drill guide, a plantar plate joint distractor, at least two K-wires, a drill bit, a graft passer, at least two interference-type screws, a screw driver, and a soft tissue graft. These components are stored in a storage container which may effectively house and store the tools necessary to provide the planter plate graft surgical procedure.

In addition, embodiments of the invention, the kit assembly provides a container to organize and carry the tools and components described herein. The container includes an outer housing and multiple inner recesses shaped and sized to frictionally fit the tools. The inner recesses help prevent inadvertent dislodging of the same while in transport or in the operating room.

In addition, embodiments of the invention provides a plantar plate drill guide that positions over the damaged area of the plantar plate. The plantar plate drill guide serves to align a drill bit and K-wires into the plantar plate during augmentation. The plantar plate drill guide includes a main body having a support member with a drill receiving platform. The support member may be disposed at a substantially orthogonal orientation with respect to the body and may be coupled to the body.

In addition, the plantar plate drill guide has a plurality of channels that may be beneficially canted at various angles to provide for various insertion angles of a removable drill insertion member and/or the drill itself.

In accordance with another feature, an embodiment of the present invention includes a plantar plate joint distractor that spreads human tissue or organs.

In accordance with another feature, the plantar plate joint distractor moves between a closed configuration and an open configuration along a spreader opening path.

In accordance with another feature, the plantar plate joint distractor is defined by two apertures to receive at least two K-wires.

In accordance with a further feature of the present invention, an embodiment of the present invention includes a drill bit being approximately 2.7 mm in diameter, and shaped and sized for insertion within the drill insertion member.

In accordance with a further feature of the present invention, an embodiment of the present invention includes a graft passer to facilitate in the handling of the graft.

In accordance with a further feature of the present invention, the graft passer has a handle end for controlling the graft passer, and a loop that retains the graft during manipulation.

In accordance with a further feature of the present invention, an embodiment of the present invention includes at least two K-wires, each approximately 0.45 inches in diameter.

In accordance with a further feature of the present invention, an embodiment of the present invention includes two interference type screws with a screw driver used in the surgical procedure.

In accordance with the present invention, a method of repairing plantar plate tears through augmentation includes an initial Step of cutting an incision above a damaged area of a plantar plate. The method may further comprise a Step of spreading the tissue at or near the plantar plate with a plantar plate joint distractor, whereby the plantar plate joint distractor is selectively expanded to an open configuration along a spreader opening path.

Another Step includes positioning a plantar drill guide over the plantar plate, the plantar drill guide comprising a main body, a support member, and a drill receiving platform, the main body being defined by a plurality of channels sloped at multiple angles. In some embodiments, a Step comprises inserting a drill insertion member into one of the channels, the selected channel being dependent on a drilling angle over the tissue. A Step includes passing a drill bit through the drill insertion member. A Step may include drilling, with the drill bit, the tissue at or near the damaged area of the plantar plate.

In some embodiments, a Step comprises positioning a graft over a damaged area of the plantar plate, whereby the graft augments the damaged area of the plantar plate. The method may further comprise a Step of passing, with a graft passer, at least two K-wires through the graft and the plantar plate. A Step includes manipulating, with a screw driver, at least two interference-type screws through the graft and the plantar plate. A final Step includes removing, after a duration, the K-wires from the plantar plate, whereby the damaged area of the plantar plate is healed.

Additionally, a method of repairing plantar plate tears of an individual through augmentation is disclosed that includes cutting an incision above a damaged area of a plantar plate on an individual, spreading the tissue at or near the plantar plate with a plantar plate joint distractor to generate an open configuration along a spreader opening path, positioning a plantar drill guide over the plantar plate, inserting a drill insertion member into the plantar drill guide and at a drilling angle over tissue at or near the damaged area of the plantar plate, drilling, with a drill bit and at the drilling angle, into the tissue at or near the damaged area of the plantar plate, attaching at least one K-wire to a graft, pulling, with the at least one K-wire, the graft across a damaged area of the plantar plate augmenting the damaged area of the plantar plate, and manipulating, with a screw driver, at least one interference-type screw through the plantar plate and either, or both, the at least one K-wire and/or the graft to engage and compress the graft for fixation.

In additional embodiments, the method may include providing the plantar drill guide with a main body defining a plurality of channels sloped at multiple different angles, a support member, and a drill receiving platform.

In further embodiments, the method may include inserting the drill insertion member into one of the plurality of channels dependent on the drilling angle over the tissue at or near the damaged area of the plantar plate.

In yet another embodiment, the method may include positioning a distal opening of the drill insertion member for receiving the drill bit to be aligned with the drill receiving platform and for drilling at the drilling angle.

In further embodiments, the method may include removing the plantar drill guide from over the plantar plate before pulling, with the at least one K-wire, the graft across a damaged area of the plantar plate augmenting the damaged area of the plantar plate.

In another embodiment, the method may include attaching at least two K-wires to the graft, pulling, with at least one of the at least one two K-wires, the graft across a damaged area of the plantar plate augmenting the damaged area of the plantar plate, and manipulating, with the screw driver, at least two interference-type screws through the plantar plate and the at least two K-wires and the graft to engage and compress the graft for fixation.

In additional embodiments, the method may include removing, after a duration, the at least two K-wires from the graft, whereby the damaged area of the plantar plate is healed.

In further embodiments, the method may include removing, after a duration, the at least one K-wire from the graft, whereby the damaged area of the plantar plate is healed.

In additional embodiments, the method may include utilizing a graft passer with a loop to manipulate the graft across the damaged area of the plantar plate augmenting the damaged area of the plantar plate, the loop retaining the graft during manipulation.

Although the invention is illustrated and described herein as embodied in a plantar plate augmentation kit assembly and method of repairing plantar plate tears through augmentation, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the assembly kit.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 9 is a perspective view of an exemplary drill bit, in accordance with the present invention;

FIG. 10 is a view of the plantar plate joint distractor, in accordance with the present invention;

FIG. 11 is a top view of an exemplary graft passer, in accordance with the present invention;

FIG. 12 is a perspective view of the graft passer, shown in FIG. 11, in accordance with the present invention;

FIG. 18 is an elevated side view of an exemplary soft tissue graft, in accordance with the present invention;

FIG. 19 is a perspective view of the soft tissue graft shown in FIG. 18, in accordance with the present invention;

FIG. 20 is a perspective view of a foot, showing the plantar fascia, plantar plate, and tendons, in accordance with the present invention;

FIG. 23 is a top perspective view of a step of the augmentation procedure, showing the plantar plate drill guide positioned over the plantar plate, in accordance with the present invention;

FIG. 24 is a perspective view of a step of the augmentation procedure, showing a graft being augmented across the damaged area of the plantar plate, in accordance with the present invention;

DETAILED DESCRIPTION

Figure 1:
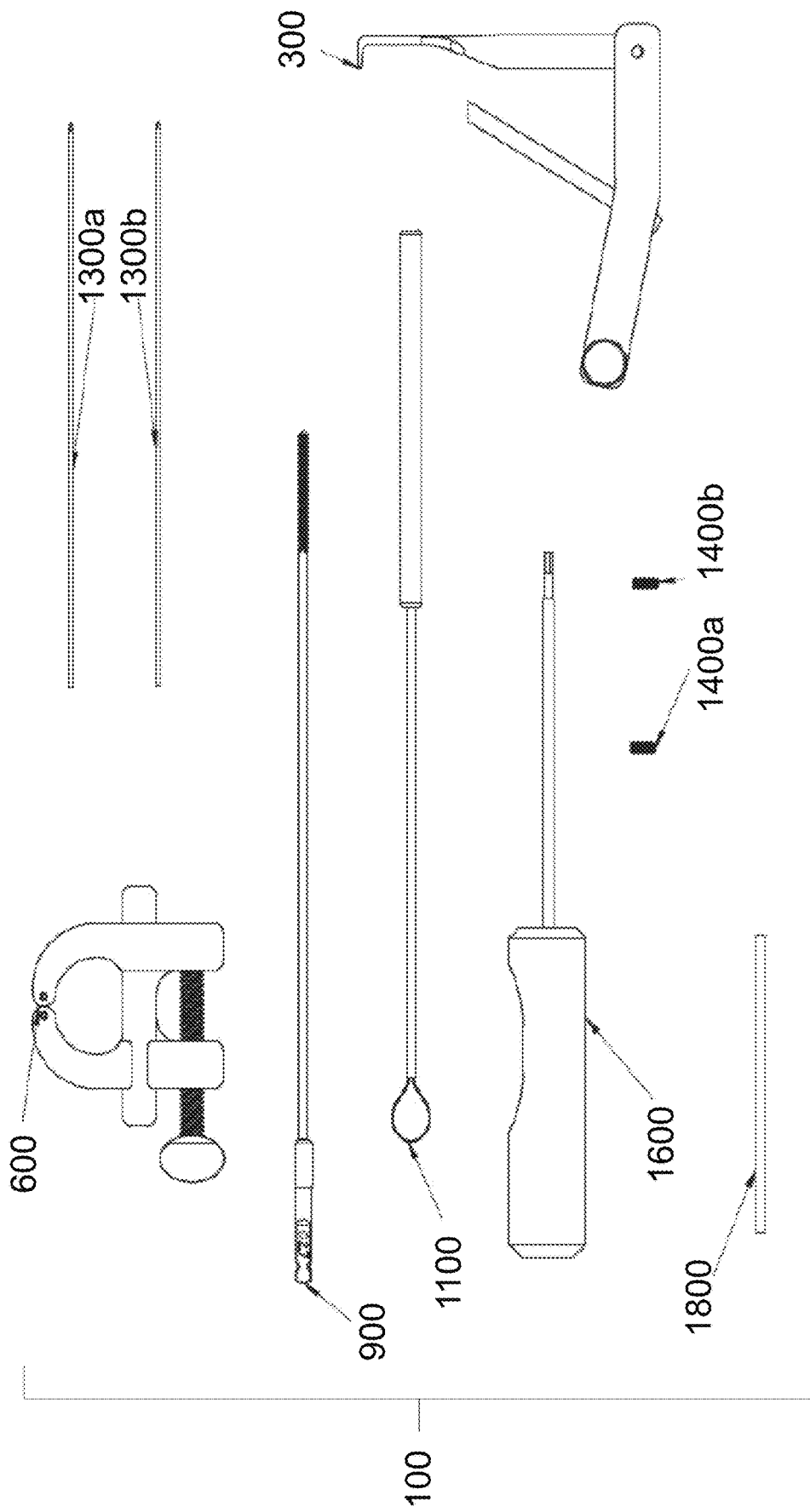
FIG. 1 is a top view of an exemplary plantar plate augmentation assembly, showing individual close-up views of the tools and/or components used in the assembly, in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient single-use assembly kit and method of use for planter plate graft augmentation. Referring now to FIG. 1, one embodiment of the present invention is shown in a perspective top angle view. FIG. 1, along with the other figures herein, shows several advantageous features of the present invention, but, as will be described below, the invention can be provided in several shapes, sizes, combinations of features and components, and varying numbers and functions of the components. The first example of a plantar plate graft augmentation assembly, as shown in FIG. 1, includes a plantar plate drill guide, a plantar plate joint distractor, at least two K-wires, a drill bit, a graft passer, at least two interference-type screws, a screw driver, and a soft tissue graft. These tools and components are stored in a storage container 200 that effectively houses and store the tools necessary to provide the planter plate graft surgical procedure.

The present invention provides a novel and efficient single-use assembly kit 100 and method 2800 of use for planter plate graft augmentation. Specifically, with reference to FIGS. 1 and 2, the assembly kit 100 provides a container, which may be designed for single use, provide instruments to perform the planter plate graft augmentation. The storage container 200 effectively houses and stores the tools necessary to provide the planter plate graft surgical procedure. In one embodiment, the container may have an outer housing 202 and multiple inner recesses 204a-n that are shaped and sized to frictionally fit the tools to prevent inadvertent dislodging of the same while in transport or in the operating room. The inner recesses 204a-n may be configured from a foam or resilient material.

The assembly kit 100 may contain a plantar plate drill guide 300 (shown in more detail in FIGS. 3-5), a plantar plate joint distractor 600 (shown in more detail in FIGS. 6-8), at least two K-wires 1300a-b (shown in more detail in FIG. 13), a drill bit 900 approximately 2.7 mm in diameter (shown in more detail in FIGS. 9-10), a graft passer 1100 (shown in more detail in FIGS. 11-12), two interference type screws 1400a-b operable with a screw driver 1600 (shown in more detail in FIGS. 14-17). The above tools are used to augment a soft tissue graft 1800 (shown in more detail in FIGS. 18-19). It is the intent of the present invention to provide a cost-effective assembly kit that is easy to use and to allow the surgeon to achieve consistent operative results.

Figure 2:
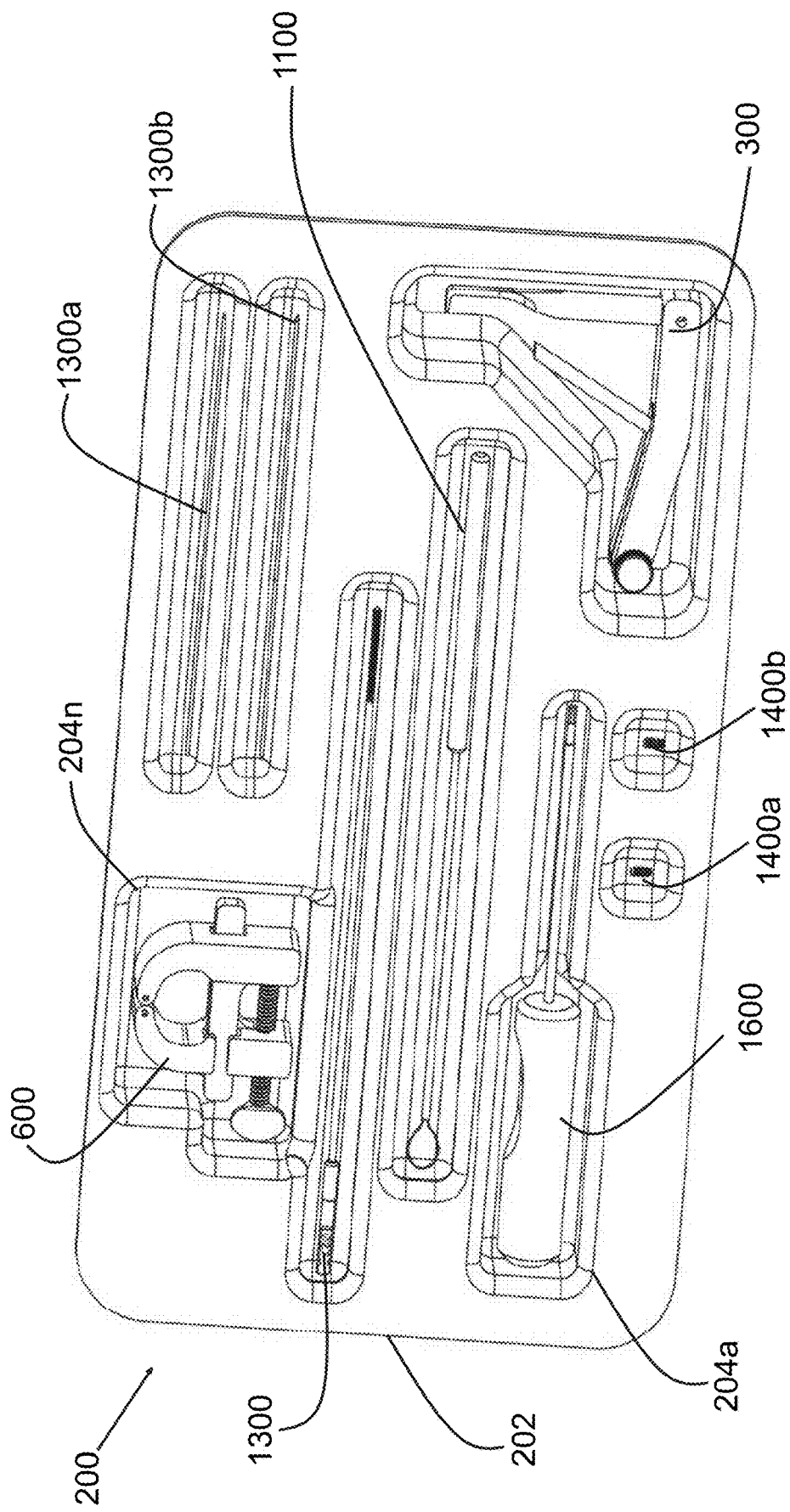
FIG. 2 is a top view of an exemplary plantar plate augmentation kit, in accordance with the present invention.

FIG. 1 references a collection of components used for the plantar plate augmentation. FIG. 2 shows a storage container 200 that store the tools. FIGS. 3-19 depict individual close-up views of the tools and/or components used in the assembly kit 100 as discussed herein. FIG. 20 references an exemplary method 2800 of use for planter plate graft augmentation.

Looking ahead to FIG. 20, it is recognized that the plantar plate 2002 is a fibrocartilaginous tissue that is the direct insertion of the plantar fascia 2000 into the base of the phalanges of the lesser toes. The plantar plate 2002 is situated on the underside of the metatarsal phalangeal joints at the ball of the feet, below the second cuneiform 2010 and the second metatarsal 2008. The plantar plate 2002 comprises an FDB tendon 2006 and an FDL tendon 2004. These tendons can tear or be strained when heavy use or loads are applied to the foot. Plantar plate 2002 injuries are a common foot condition that has been a challenging procedure for physicians to master. Traditionally, there are complicated suture based repair techniques that are difficult to perform and are based on a suture repair, and not graft augmentation.

To aid in overcoming surgical challenges associated with plantar plate injuries, the present invention provides a planter plate graft augmentation kit 100 and method 2800 of use. Specifically, in one embodiment, the kit described below, which may be designed for single use by a physician, is designed to provide a surgeon a fast, easy, and effective way to repair the plantar plate tear. This technique uses an FDA approved soft tissue graft that augments the plantar plate structure, and specifically for reinforcement and augmentation of tissue repair, e.g., ligaments, tendons, general soft tissues.

Those skilled in the art will recognize that tendons are tough, fibrous bands of tissue that attach muscles to bones. Tendons can become torn or frayed because of overuse or injury. The graft tissue used in the present invention is efficacious for protecting and reinforcing a damaged tendon in the plantar plate, helping it heal. In one non-limiting embodiment, the graft used is an FDA approved Artelon graft. The Artelon graft may be of a porous polyurethane material and acts as a scaffold which promotes ingrowth of native human tissue. Typically, the Artelon graft degrades over a period of around 5-7 years during which time most of the material is replaced by native human tissue.

Figure 3:
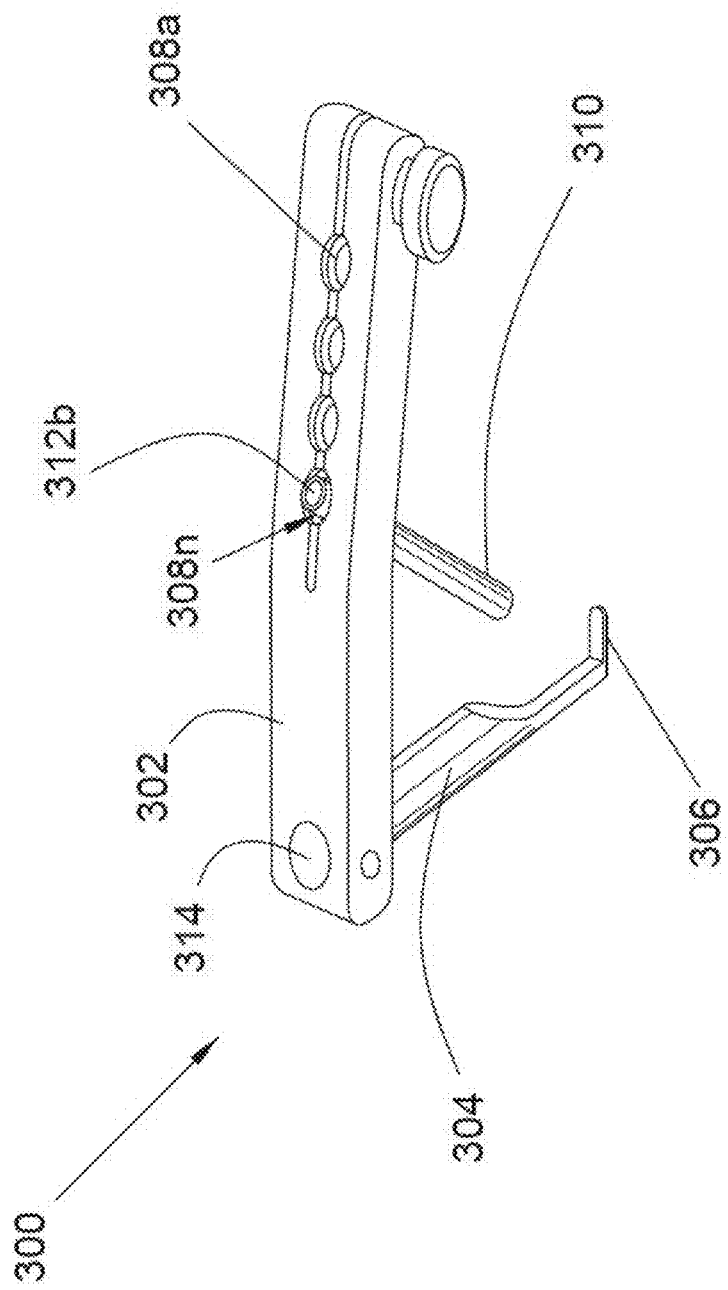
FIG. 3 is a perspective view of an exemplary plantar plate drill guide, in accordance with the present invention.

With reference specifically to FIG. 3, an exemplary and unique plantar plate drill guide 300 is shown. The plantar plate drill guide 300 is used to position over a damaged area of a plantar plate 2002, so as to align a drill for drilling therein. The plantar plate drill guide 300 comprises a main body 302 that is flat and linear. The main body 302 is defined by multiple channels 308*a-n*. The channels may have a circular shape to accommodate a circular drill, as described below.

Figure 4:
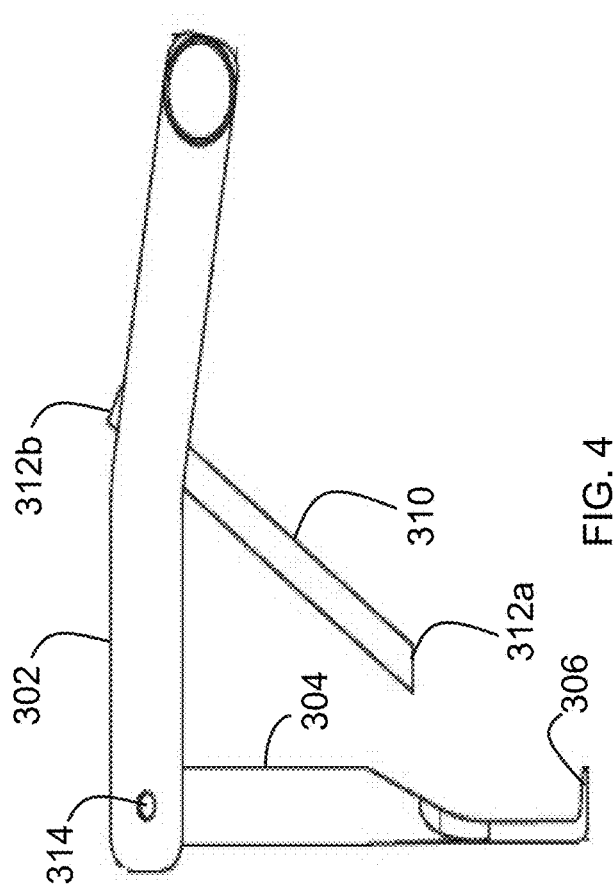
FIG. 4 is an elevated side view of the plantar plate drill guide, shown in FIG. 3, in accordance with the present invention.

The plantar plate drill guide 300 also includes a support member 304 is disposed at a substantially orthogonal orientation with respect to the main body 302 (FIG. 4). The support member 304 holds the main body 302 and channels 308*a-n* over a damaged area of the plantar plate 2002. In this manner, the channel, and the drill therein is oriented to a desired angle. The support member 304 is coupled to the main body 302 using a fastener 314, adhesive, or compression fitting.

Figure 5:
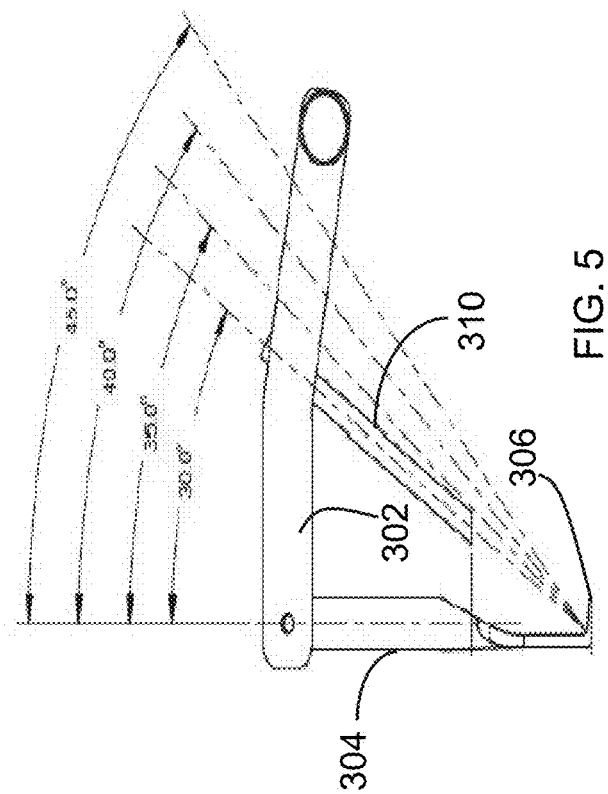
FIG. 5 is a perspective view of the plantar plate drill guide, showing the removable drill insertion member pivoting at different angles, in accordance with the present invention.

Looking now at FIG. 5, the plantar plate drill guide 300 further provides a support member 304 that includes a drill receiving platform 306. The channels 308*a-n* may be beneficially canted at various angles to provide various insertion angles of a removable drill insertion member 310 and/or a drill bit 900. This allows drilling into the plantar plate 2002 at incremental angles.

The drill insertion member 310 is a hollow cylindrical piece that may be removably couplable to the channels in the main body 302 using friction fitting and/or a fastener. The drill insertion member 310 can be seen defining the channel that accommodates a drill used in connection with the surgical procedure. The drill insertion member 310 may include a hollow body having a proximal opening 312*a* and distal opening 312*b*.

The orientation of the drill insertion member 310, particularly the distal opening 312*b*, provides an inlet for a drill bit 900 or other drilling device to be aligned with the receiving drill receiving platform 306. Once the drill bit passes through, a drill can then rotate the drill bit at the desired angle of the selected channel 308*a*. This allows for drilling at or near the damaged area of the plantar plate in a precise manner.

Figure 6:
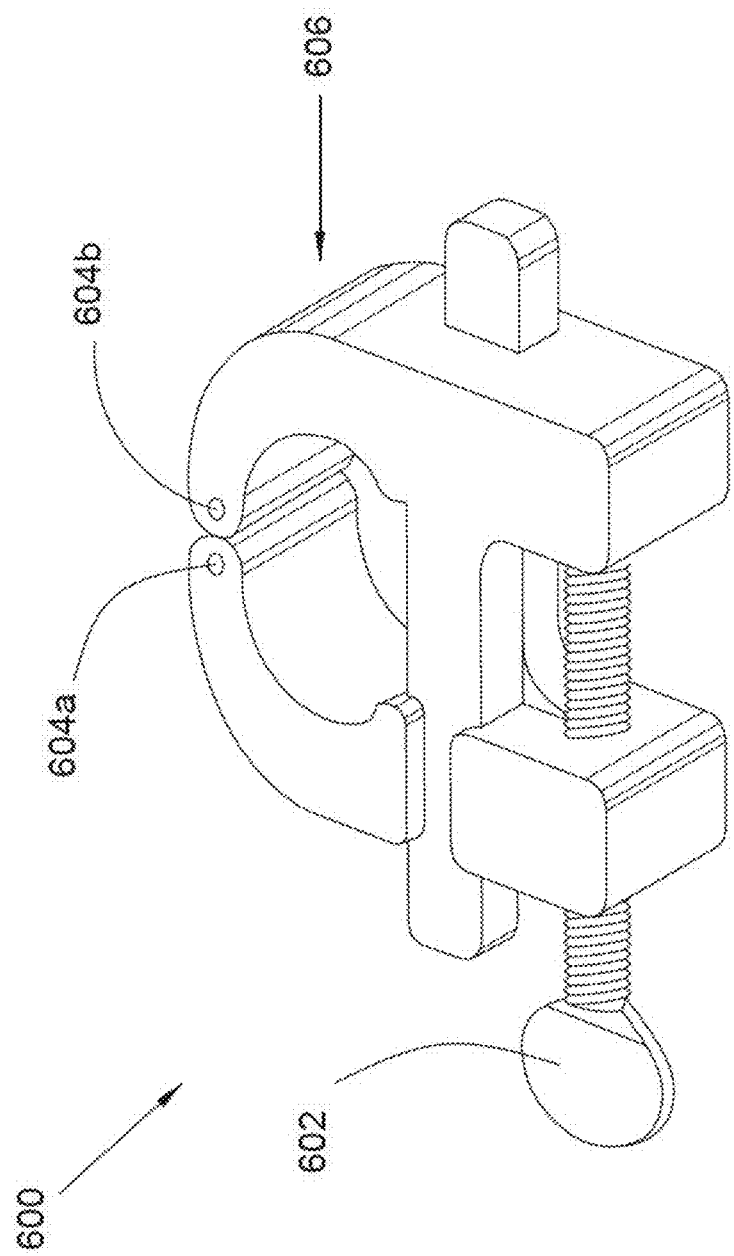
FIG. 6 is a perspective view of an exemplary plantar plate joint distractor, in accordance with the present invention.
Figure 8:
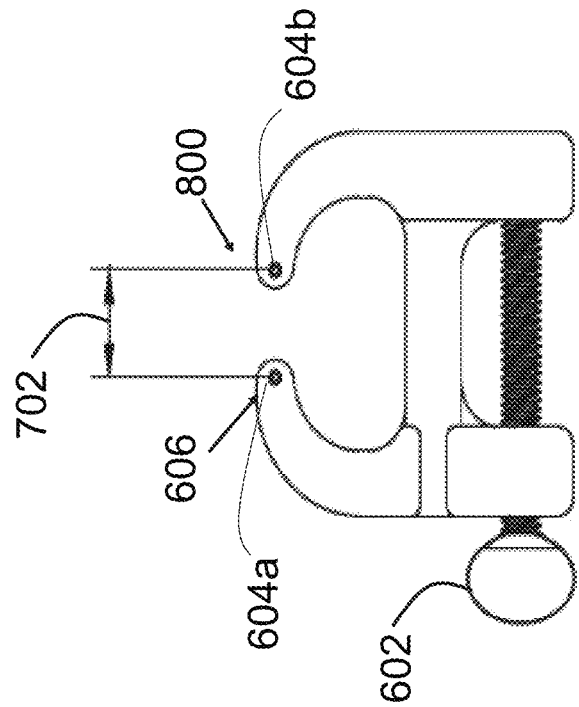
FIG. 8 is a perspective view of the plantar plate joint distractor, shown in FIG. 6 in an open position, in accordance with the present invention.
Figure 7:
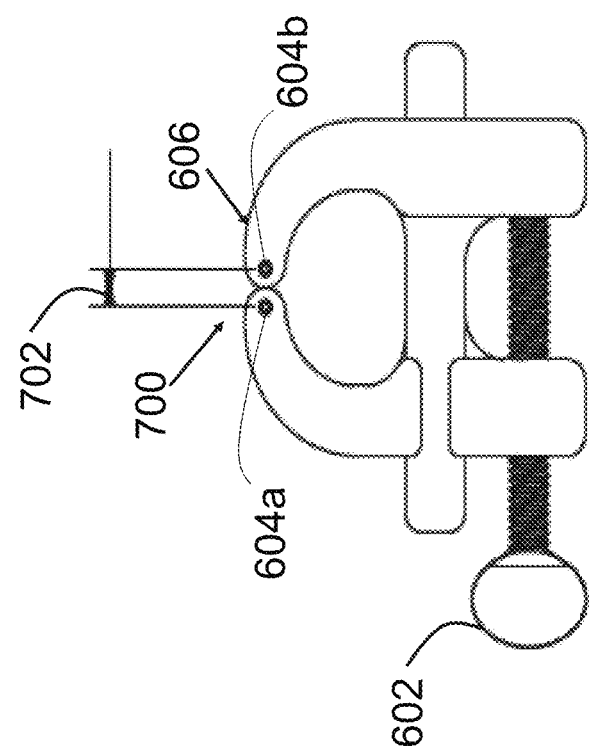
FIG. 7 is a perspective view of the plantar plate joint distractor, shown in FIG. 6 in a closed position, in accordance with the present invention.

With reference specifically to FIG. 6, an exemplary plantar plate joint distractor 600 can be seen. As will be appreciated by those of skill in the art, the plantar plate joint distractor 600 can be utilized to spread muscle or other human tissue. The plantar plate joint distractor 600 is configured to expand and retract sections of tissue at or near the plantar plate. FIG. 7 depicts the plantar plate joint distractor 600 in a closed configuration 700 along a spreader opening path 702, while FIG. 8 depicts the plantar plate joint distractor 600 in an open configuration 800 along the spreader opening path 702.

In some embodiments, the plantar plate joint distractor 600 may be mechanically or electro-mechanically placed in the spreader opening path 702 using, for example, a bolt-thread mechanism 602. The bolt-thread mechanism 602 may include a threaded lever that moves a pair of clamps distally and proximally relative to each other. The plantar plate joint distractor 600 can also be seen having two apertures 604*a*, 604*b* disposed toward the distal ends 606 of the plantar plate joint distractor 600, which are configured to receive at least two K-wire, described below.

With reference specifically to FIGS. 9-10, the kit assembly 100 also includes a drill bit 900. The drill bit 900 is used to drive the graft into position at the damaged area of the plantar plate 2002 (See FIG. 27). The drill bit 900 may also be used to remove tissue material and form a hole at or near the damaged area of the plantar plate. The drill bit 900 is defined by a body portion 902 that terminates at a drill head 906. The body portion 902 is approximately 2.7 mm in diameter. However, in other embodiments, larger or smaller diameters, however, may be utilized. The chuck end 904 of the drill bit 900 may be shaped and sized for insertion within the drill insertion member 310. A power drill then couples to the check end 904 of the drill bit 900 for driving into the plantar plate.

With reference specifically to FIGS. 11-12, a graft passer 1100 is employed to facilitate in the handling of a soft tissue graft 1800, e.g., an Artelon Graft (shown in FIGS. 18-19). The graft passer 1100 has a handle end 1102 for controlling the graft passer 1100, and a loop 1104 that retains the graft 1800 during manipulation. The loop shape of the graft passer 1100 encircles the graft 1800 for alignment across the damaged area of the plantar plate during augmentation thereof.

Figure 13:
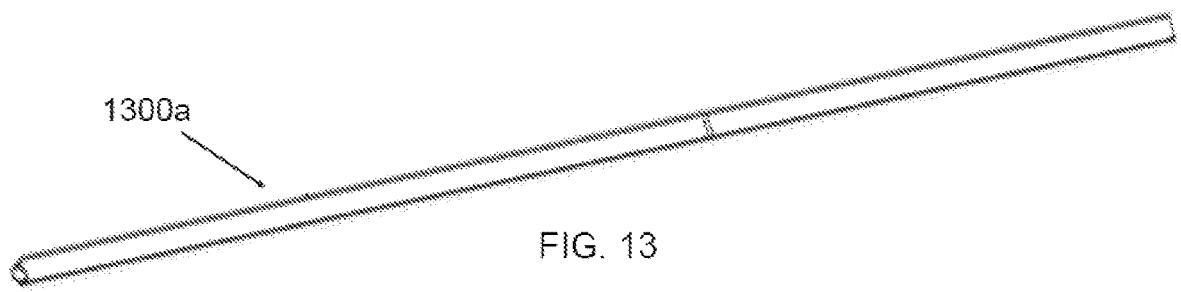
FIG. 13 is a perspective view of a K-wire, in accordance with the present invention.

With reference specifically to FIG. 13, the kit assembly 100 provides at least two K-wires 1300a, 1300b that attach to the graft, so as to help manipulate the graft to the desired position across the damaged plantar plate 2002. The K-wires 1300a-b may also be driven into the tissue of the plantar plate for retaining the augmented tissue in the desired position; serving as anchors therein. The K-wires 1300a-b are anchored from one end to the apertures 604a-b in the distal end 606 of the plantar plate joint distractor 600. In this manner, moving the plantar plate joint distractor 600 between the open and closed configurations 800, 700 works to adjust the positon of the K-wires 1300a-b.

The K-wires 1300a-b may also include Kirschner wires. The two K-wire 1300a-b may be each approximately 0.45" in diameter. Though in alternative embodiments, greater or smaller diameters may be used. K-wires 1300a-b can also be considered to be a pin. In one non-limiting embodiment, the K-wire 1300a-b is a section of sterilized, sharpened, smooth stainless steel pin.

Figure 14:
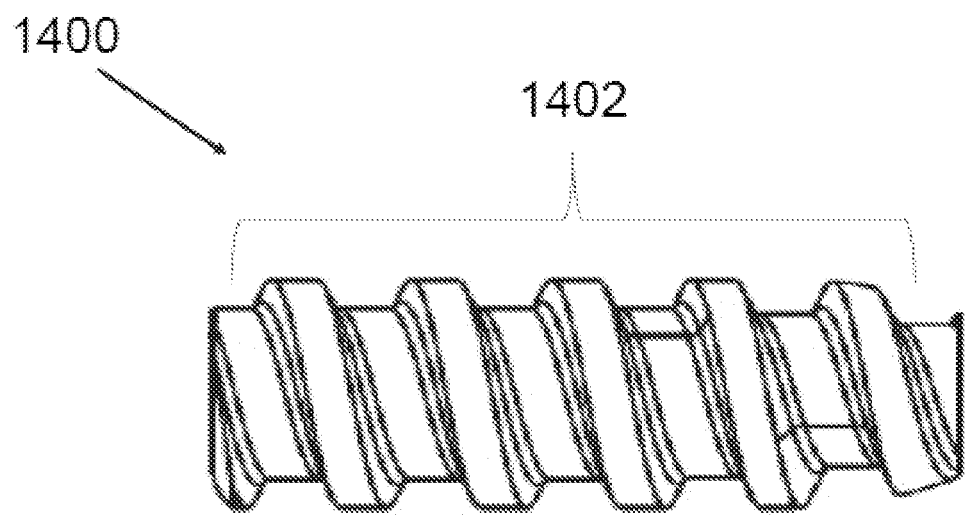
FIG. 14 is an elevated side view of an exemplary interference type screw, in accordance with the present invention.
Figure 15:
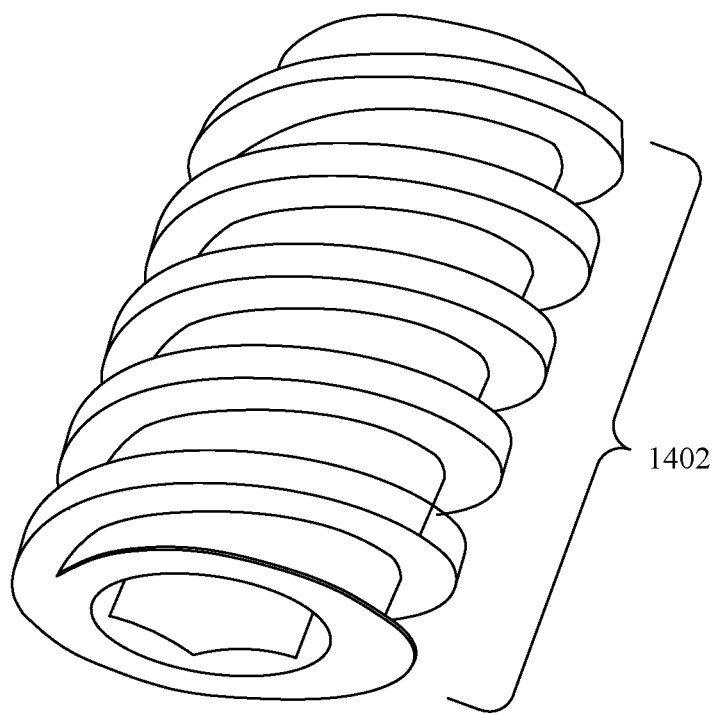
FIG. 15 is a perspective view of an interference type screw, in accordance with the present invention.

With reference specifically to FIGS. 14-15, the kit assembly also provides two interference type screws 1400a, 1400b. The interference type screws 1400a, 1400b provide a direct tendon-to-bone interference fixation device for securing the K-wires 1300a-b and graft 1800 into place. The interference type screws 1400a, 1400b are defined by screw threads 1402 that engage and compress the graft 1800 for fixation.

Figure 16:
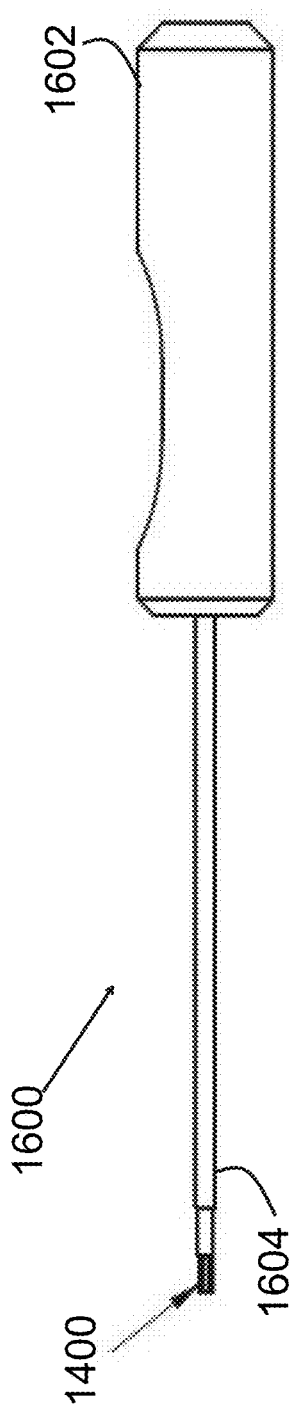
FIG. 16 is an elevated side view of an exemplary screw driver manipulating the interference type screw, in accordance with the present invention.
Figure 17:
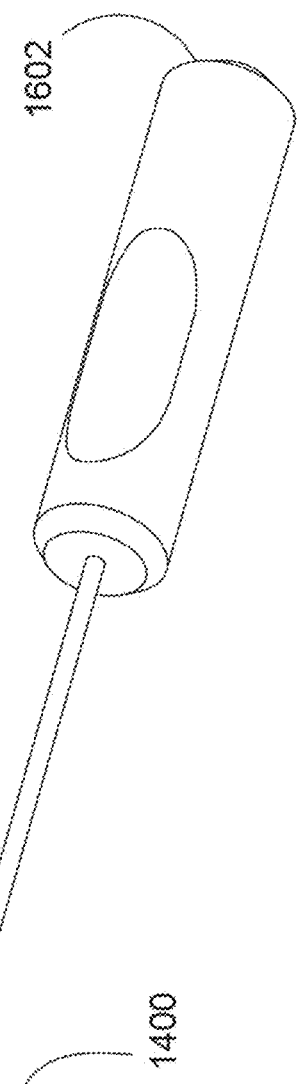
FIG. 17 is a perspective view of an exemplary screw driver manipulating the interference type screw, in accordance with the present invention.

As FIGS. 16-17 show, the kit assembly 100 also provides a screw driver 1600 defined by a proximal end 1602 and a distal end 1604. The interference type screws 1400a, 1400b detachably attach to the distal end 1604 of the screw driver 1600, such that the screw driver manipulates and inserts the interference type screws 1400a, 1400b through the graft 1800 and K-wire ends during the surgical procedure.

Figure 27:
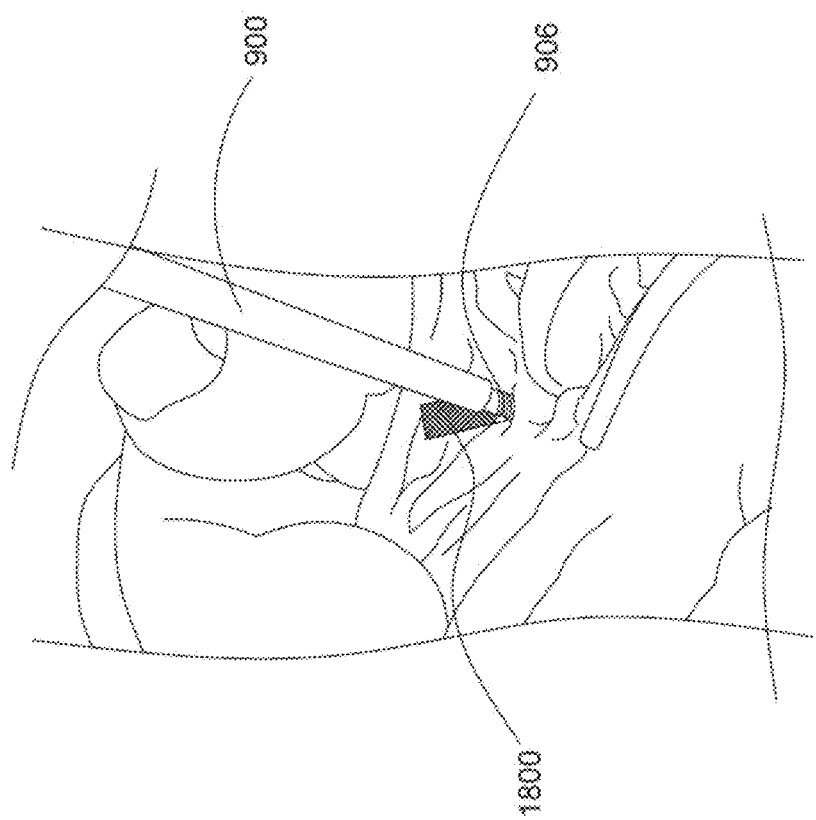
FIG. 27 is a perspective view of a step of the augmentation procedure, showing a drill driving the graft into the plantar plate, in accordance with the present invention.
Figure 28:
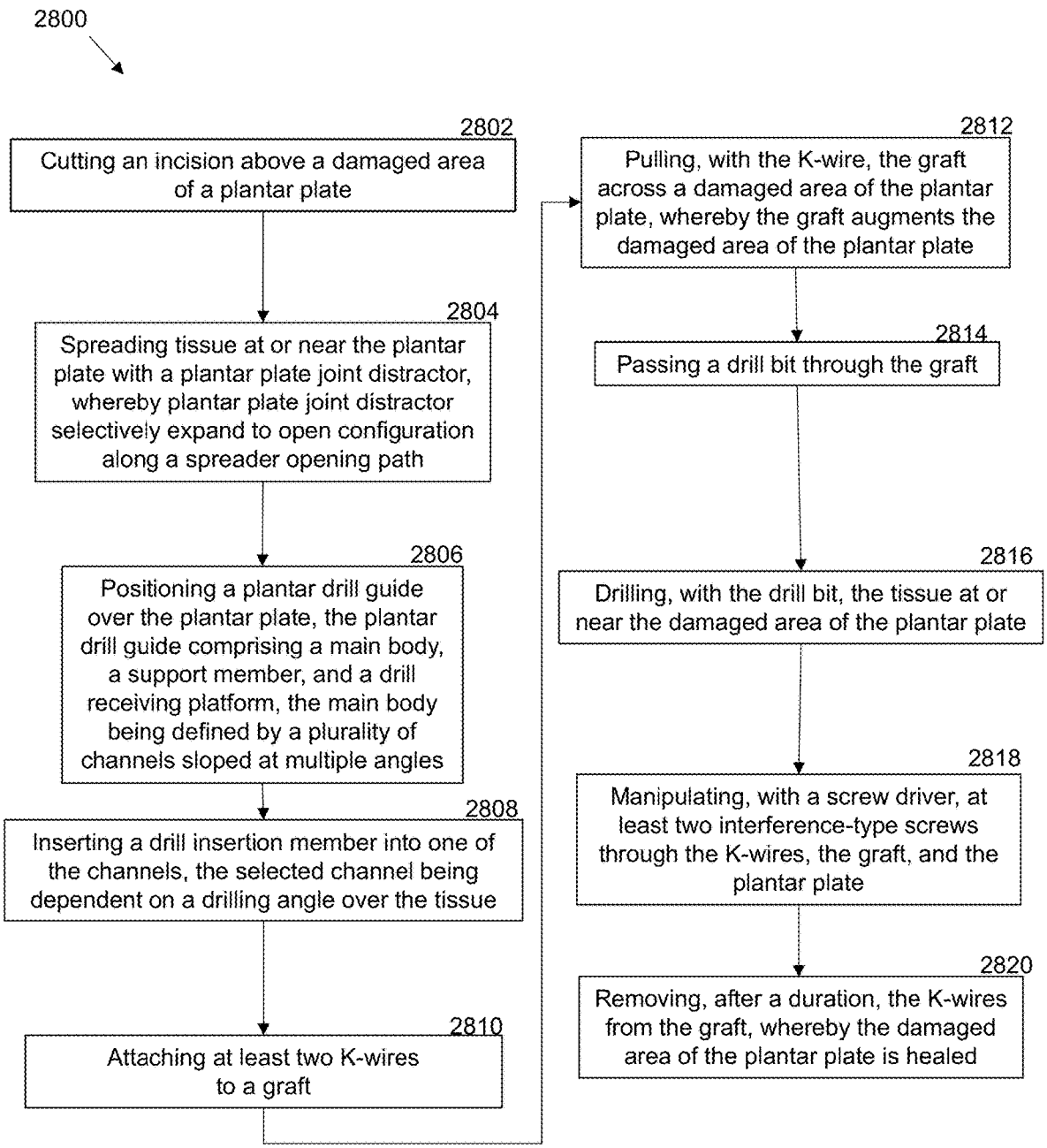
FIG. 28 illustrates a flowchart of an exemplary method of repairing plantar plate tears through augmentation, in accordance with the present invention.

FIGS. 1-27 are described in conjunction with the process flow chart of FIG. 28. Although FIG. 28 shows a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIG. 28 for the sake of brevity. In some embodiments, some or all of the process steps included in FIG. 28 can be combined into a single process.

Figure 21:
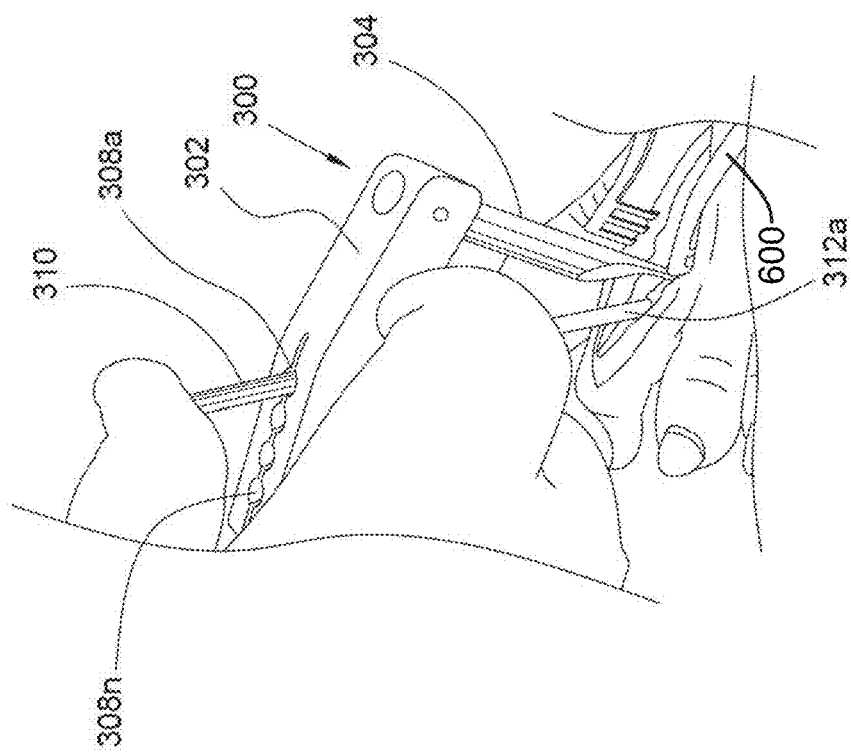
FIG. 21 is a perspective view of one step of the augmentation procedure, showing the plantar plate joint distractor separating skin to access the damaged area of the plantar plate, in accordance with the present invention.

In some embodiments, a method 2800 of repairing plantar plate tears through augmentation includes an initial Step 2802 of cutting an incision above a damaged area of a plantar plate. The area is marked prior to cutting in order to determine the appropriate incision location. The method 2800 may further comprise a Step 2804 of spreading the tissue at or near the plantar plate with a plantar plate joint distractor 600, whereby the plantar plate joint distractor is selectively expanded to an open configuration 800 along a spreader opening path 702. FIG. 21 illustrates the plantar plate joint distractor 600 separating the skin to expose the damaged tendons at or near the plantar plate 2002. A bolt mechanism 602 can be manually turned to urge the plantar plate joint distractor 600 between the open and closed positions.

Figure 22:
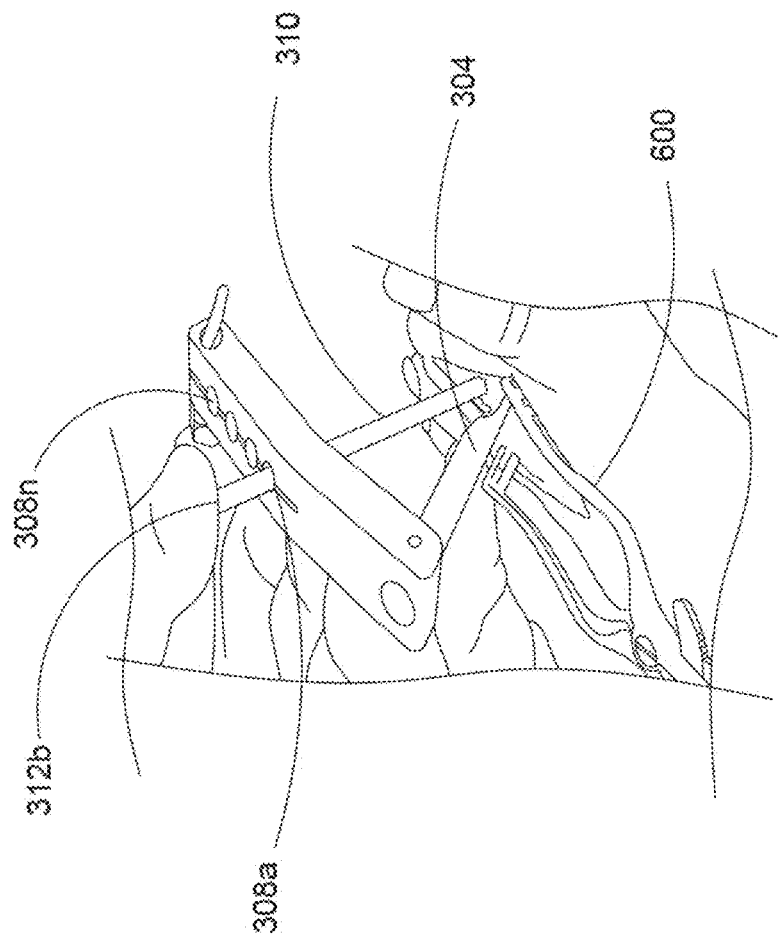
FIG. 22 is a side perspective view of a step of the augmentation procedure, showing the plantar plate drill guide positioned over the plantar plate, in accordance with the present invention.

As illustrated in FIG. 22, a Step 2806 includes positioning a plantar drill guide over the plantar plate, the plantar drill guide comprising a main body, a support member, and a drill receiving platform, the main body being defined by a plurality of channels sloped at multiple angles. The plantar plate drill guide 300 is used to position over a damaged area of a plantar plate, so as to align a drill for drilling therein. The drill insertion member fits into the appropriate channel to guide the drill bit into the tissue (FIG. 23).

Figure 25:
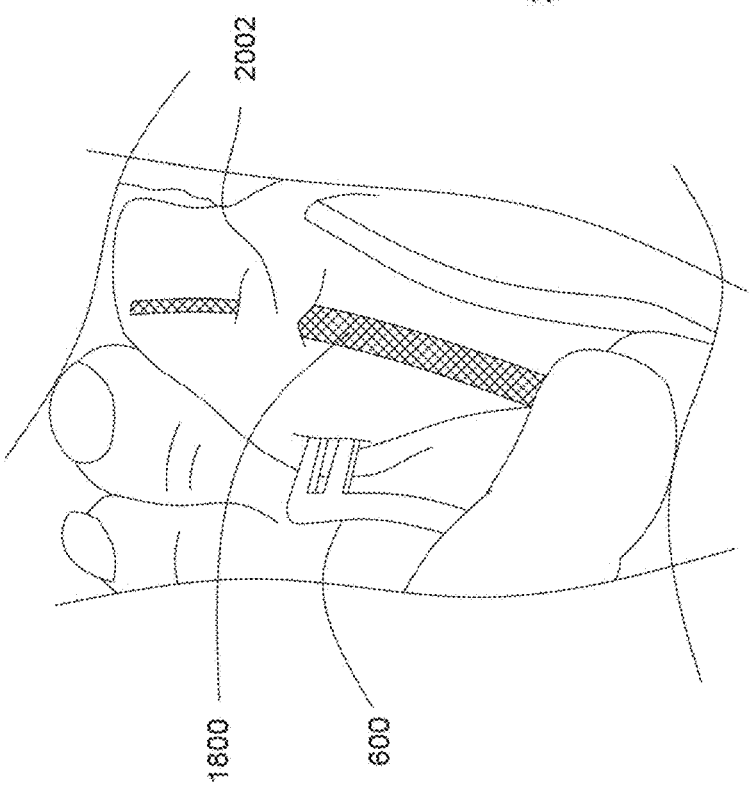
FIG. 25 is a perspective view of a step of the augmentation procedure, showing the graft being manipulated across the plantar plate, in accordance with the present invention.

In some embodiments, a Step 2808 comprises inserting a drill insertion member into one of the channels, the selected channel being dependent on a drilling angle over the tissue. The drill insertion member is a cylindrical component that helps guide the drill to the appropriate location above the plantar plate 2002. A Step 2810 includes attaching at least two K-wires to a graft (FIG. 24). The graft is an FDA approved soft tissue graft, including an Artelon graft. The K-wire is used to pull and manipulate the graft to the desired position across the damaged area of the plantar plate 2002. FIG. 25 shows the graft positioned across the plantar plate, serving as an augmentation thereof. At this stage of the procedure, the plantar plate drill guide has been removed to provide space to manipulate the graft.

Figure 26:
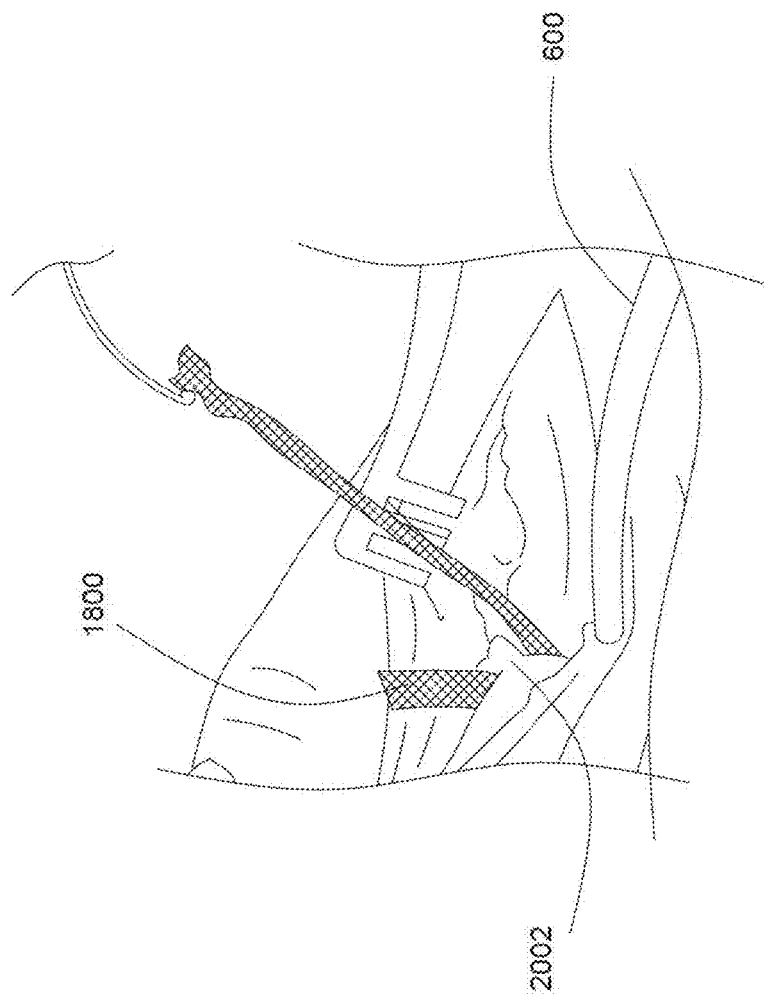
FIG. 26 is a perspective view of a step of the augmentation procedure, showing a K-wire pulling the graft across the plantar plate, in accordance with the present invention.

Turning now to FIG. 26, a Step 2812 may include pulling, with the K-wire, the graft across a damaged area of the plantar plate, whereby the graft augments the damaged area of the plantar plate. As shown in FIG. 27, a Step 2814 comprises passing a drill bit through the graft. The drill bit drives the graft across the damaged area of the plantar plate. The method may further comprise a Step 2816 of drilling, with the drill bit, the tissue at or near the damaged area of the plantar plate. Once manipulated to the desired positon for augmentation, the ends of the K-wires can be drilled into the tissue, serving as an anchor thereto.

In some embodiments, the method 2800 further includes a Step 2818 includes manipulating, with a screw driver, at least two interference-type screws through the K-wires, the graft, and the plantar plate. A final Step 2820 includes removing, after a duration, the K-wires from the graft, whereby the damaged area of the plantar plate is healed.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

These and other advantages of the invention will be further understood and appreciated by those skilled in the art by reference to the following written specification, claims and appended drawings. Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method of repairing plantar plate tears of an individual through augmentation comprising the steps of:
   cutting an incision above a damaged area of a plantar plate on an individual;
   spreading the tissue at or near the plantar plate with a plantar plate joint distractor to generate an open configuration along a spreader opening path;
   positioning a plantar drill guide over the plantar plate;
   inserting a drill insertion member into the plantar drill guide and at a drilling angle over tissue at or near the damaged area of the plantar plate;

drilling, with a drill bit and at the drilling angle, into the tissue at or near the damaged area of the plantar plate;

attaching at least one K-wire to a graft;

pulling, with the at least one K-wire, the graft across a damaged area of the plantar plate augmenting the damaged area of the plantar plate; and manipulating, with a screw driver, at least one interference-type screw through the plantar plate and at least one of the at least one of the K-wire and the graft to engage and compress the graft for fixation.

2. The method according to claim 1, further comprising:

providing the plantar drill guide with a main body defining a plurality of channels sloped at multiple different angles, a support member, and a drill receiving platform.

3. The method according to claim 2, further comprising:

inserting the drill insertion member into one of the plurality of channels dependent on the drilling angle over the tissue at or near the damaged area of the plantar plate.

4. The method according to claim 3, further comprising:

positioning a distal opening of the drill insertion member for receiving the drill bit to be aligned with the drill receiving platform and for drilling at the drilling angle.

5. The method according to claim 1, further comprising:

removing the plantar drill guide from over the plantar plate before pulling, with the at least one K-wire, the graft across a damaged area of the plantar plate augmenting the damaged area of the plantar plate.

6. The method according to claim 1, further comprising:

attaching at least two K-wires to the graft;

pulling, with at least one of the at least one two K-wires, the graft across a damaged area of the plantar plate augmenting the damaged area of the plantar plate; and manipulating, with the screw driver, at least two interference-type screws through the plantar plate and the at least two K-wires and the graft to engage and compress the graft for fixation.

7. The method according to claim 6, further comprising:

removing, after a duration, the at least two K-wires from the graft, whereby the damaged area of the plantar plate is healed.

8. The method according to claim 1, further comprising:

removing, after a duration, the at least one K-wire from the graft, whereby the damaged area of the plantar plate is healed.

9. The method according to claim 1, further comprising:

utilizing a graft passer with a loop to manipulate the graft across the damaged area of the plantar plate augmenting the damaged area of the plantar plate, the loop retaining the graft during manipulation.

\* \* \* \* \*